US012571769B2

(12) United States Patent
Maurice et al.

(10) Patent No.: US 12,571,769 B2
(45) Date of Patent: Mar. 10, 2026

(54) PROBE FOR MEASURING VISCOELASTIC PROPERTIES OF A MEDIUM OF INTEREST

(71) Applicant: E-SCOPICS, Aix-en-Provence (FR)

(72) Inventors: Francois Maurice, Draguignan (FR);
Pascal Bouscasse, Saint-Esteve-Janson (FR); Claude Cohen-Bacrie, Aix-en-Provence (FR); Frederic Wintzenrieth, Aix-en-Provence (FR); Adrien Besson, Marseilles (FR)

(73) Assignee: E-SCOPICS, Aix-en-Provence (FR)

( * ) Notice: Subject to any disclaimer, the term of this patent is extended or adjusted under 35 U.S.C. 154(b) by 217 days.

(21) Appl. No.: 18/249,897

(22) PCT Filed: Oct. 22, 2021

(86) PCT No.: PCT/EP2021/079332
§ 371 (c)(1),
(2) Date: Apr. 20, 2023

(87) PCT Pub. No.: WO2022/084502
PCT Pub. Date: Apr. 28, 2022

(65) Prior Publication Data
US 2024/0011947 A1     Jan. 11, 2024

(30) Foreign Application Priority Data

Oct. 22, 2020     (FR) ....................................... 2010857

(51) Int. Cl.
*G01N 29/04*       (2006.01)
*G01N 33/483*      (2006.01)

(52) U.S. Cl.
CPC ....... *G01N 29/045* (2013.01); *G01N 33/4833* (2013.01); *G01N 2291/02475* (2013.01);
(Continued)

(58) Field of Classification Search
None
See application file for complete search history.

(56) References Cited

U.S. PATENT DOCUMENTS

| 7,901,355 B2 | 3/2011 | Querleux et al. |
| 11,331,073 B2 | 5/2022 | Sandrin |

(Continued)

FOREIGN PATENT DOCUMENTS

| EP | 1531733 A2 | 5/2005 |
| EP | 3315074 A1 | 5/2018 |

(Continued)

OTHER PUBLICATIONS

International Preliminary Report on Patentability received for PCT Patent Application No. PCT/EP2021/079332, mailed on May 4, 2023, 15 pages (8 pages of English Translation and 7 pages of Original Document).
International Search Report and Written Opinion received for PCT Patent Application No. PCT/EP2021/079332, mailed on Feb. 11, 2022, 18 pages (8 pages of English Translation and 10 pages of Original Document).

(Continued)

*Primary Examiner* — Suman K Nath
(74) *Attorney, Agent, or Firm* — WOMBLE BOND DICKINSON (US) LLP

(57)     ABSTRACT

A probe for measuring the viscoelastic properties of a medium of interest, the probe including a housing, a transducer array for emitting high-frequency ultrasonic waves and receiving acoustic echoes, at least one inertial vibration exciter including a fixed part mechanically integral with the transducer array, a mobile part capable of moving relative to the fixed part to produce vibrations in order to generate the low-frequency elastic wave, wherein the mobile part includes at least one permanent magnet, the at least one inertial vibration exciter including an additional inertial mass distributed around the permanent magnet.

9 Claims, 8 Drawing Sheets

(52) U.S. Cl.
    CPC .............. *G01N 2291/02818* (2013.01); *G01N 2291/106* (2013.01)

(56) References Cited

U.S. PATENT DOCUMENTS

| | | | | |
|---|---|---|---|---|
| 2004/0066313 A1* | 4/2004 | Ong | ....................... | G08C 19/04 |
| | | | | 340/870.11 |
| 2014/0097562 A1* | 4/2014 | Boechler | ................. | F16F 9/303 |
| | | | | 267/140.13 |
| 2019/0231318 A1 | 8/2019 | Audiere et al. | | |

FOREIGN PATENT DOCUMENTS

| | | | |
|---|---|---|---|
| FR | 2843290 A1 | 2/2004 |
| WO | 2004/016176 A2 | 2/2004 |
| WO | 2010/007234 A1 | 1/2010 |
| WO | 2010/063951 A1 | 6/2010 |

OTHER PUBLICATIONS

Sandrin et al., "Shear Elasticity Probe for Soft Tissues with 1-D Transient Elastography", IEEE Transactions on Ultrasonics, Ferroelectrics, and Frequency Control, vol. 49, No. 4, Apr. 2002, pp. 436-446.

Sandrin et al., "Shear Modulus Imaging with 2-D Transient Elastography", IEEE Transactions on Ultrasonics, Ferroelectrics, and Frequency Control, vol. 49, No. 4, Apr. 2002, pp. 426-435.

Mellema, Daniel C., et al., "Probe Oscillation Shear Elastography (PROSE): A High Frame-Rate Method for Two-Dimensional Ultrasound Shear Wave Elastography," IEEE Trans Med Imaging. Sep. 2016 ; 35(9): 2098-2106.

Azar, Reza Zahiri, et al., "Real-Time Transient Elastography on Standard Ultrasound Using Mechanically Induced Vibration: System Design and Initial Results," 2011 IEEE International Ultrasonics Symposium Proceedings p. 2388 2391.

* cited by examiner

PROBE FOR MEASURING VISCOELASTIC PROPERTIES OF A MEDIUM OF INTEREST

FIELD OF THE INVENTION

The present invention relates to the general technical field of imaging a target object, or a diffuse medium such as a human or animal biological tissue.

More specifically, the present invention relates to a device and a method for measuring viscoelastic properties of a biological tissue of interest.

It applies in particular, but not exclusively, to the measurement of viscoelasticity parameters of the liver of a human or an animal, this measurement being correlated with the amount of fibrosis present in the liver.

BACKGROUND OF THE INVENTION

In order to measure the tissue viscoelastic properties, it is known to use shear wave elastography.

This technique consists in measuring the speed of propagation of a shear wave in a tissue, this speed being directly related to the viscoelastic properties of the analyzed tissue.

The shear wave can be generated:
either by mechanical stress,
or by acoustic stress.

1. Mechanical Shear Wave Generation

To estimate the viscoelastic properties of a tissue, an ultrasonic pulse elastography medical apparatus, called Fibroscan®, has already been proposed.

With reference to FIG. 1, this apparatus 1 comprises:
an ultrasonic transducer 11 for the emission of ultrasonic waves and the acquisition of echoes,
an electrodynamic actuator 12 forming a vibrator,
a housing (not shown) containing the electrodynamic actuator 12.

The transducer 11 is attached to the end of the electrodynamic actuator 12. The electrodynamic actuator 12 allows to vibrate the transducer 11 to generate a shear wave. The principle of operation of the medical pulse elastography apparatus 1 is as follows.

The electrodynamic actuator 12 is activated to induce the movement of the transducer 11 and generate a low-frequency shear wave in the tissue to be analyzed. During the propagation of the low-frequency shear wave, the transducer 11 emits and receives high-frequency ultrasonic waves in order to allow the study of the propagation of the low-frequency shear wave.

The mode of generation of the shear wave proposed above is relatively effective in the transmission of mechanical energy to the tissue, since the ultrasonic transducer 11, in contact with the tissue, is directly moved by the electrodynamic actuator 12 held by the user.

However, a disadvantage of this technology is that it is unsuitable for two-dimensional (2D) mapping of a tissue. Indeed, the 2D mapping of a tissue requires the use of an ultrasonic transducer array. However, it is difficult (if not impossible) to attach such a transducer array to the end of an electrodynamic actuator due to:
its dimensions on the one hand (which can be 60×15 mm), and
of the bundle of cables connected to the transducers of the array on the other hand.

It has also been proposed (in the document entitled "*Shear Modulus Imaging with 2-D Transient Elastography*" by Sandrin published in 2002) to separate the mechanical excitation from the ultrasonic probe. In particular, FIG. 2 illustrates a pulse elastography system 2 including:
mechanical excitation means (forming a vibrator) for the generation of a low-frequency elastic shear wave in the tissue, and
means for generating high-frequency ultrasonic waves for imaging the tissue, the wave generating means being separated from the mechanical excitation means.

In particular, the mechanical excitation means of the system include two bars 24 the movements of which are controlled by two magnetic electro-vibrators 22. The ultrasonic wave generation means in turn include a set of transduction elements 23 (composed of 128 elements) allowing to image the tissue to study the propagation of the elastic shear wave generated by the mechanical excitation means. The set of transducer elements 23 is disposed between the two bars 24.

This system allows the production of a 2D mapping during the estimation of the viscoelastic properties of a tissue. However, its design has many disadvantages. In particular, the positioning of the bars 24 on either side of the set of transduction elements 23:
induces a large width for the mechanical excitation means which makes the system 2 incompatible with an exploration of the liver between the ribs of a patient,
can, moreover, pose problems of disinfection of the system 2.

More recently, document EP 3 315 074 has proposed a probe for transient elastography comprising:
a housing,
one (or more) ultrasonic transducer(s) having an axis of symmetry A,
one (or more) vibrator(s), each vibrator being located inside the housing,
a position sensor coupled to the housing,
a feedback circuit.

The position sensor is arranged to measure the movement of the probe. The vibrator is able to vibrate in a frequency range comprised between 1 Hz and 5 kHz. It is made up of a fixed part and a mobile part whose mass is greater than or equal to 25% of the total mass of the probe. The mobile part is able to move in translation along a guide rod. This vibrator is arranged to induce a movement of the housing along the axis of symmetry A of the ultrasonic transducer. The feedback circuit uses the movement of the probe to control the movement of the vibrator(s) inside the housing and the shape of a low-frequency pulse applied by the probe.

A disadvantage of the probe described in EP 3 315 074 relates to its large size. Another disadvantage of the probe according to EP 3 315 074 relates to the high electrical energy consumption of the vibrator, which makes this probe unsuitable for a battery power supply. Finally, the damping of the vibrations generated by the vibrator(s) can vary depending on the orientation of the probe.

2. Acoustic Shear Wave Generation

To overcome the disadvantages of the aforementioned apparatus 1 and system 2, it has been proposed to generate the shear wave using acoustic means rather than mechanical means.

Different solutions based on ultrasonic radiation pressure (which consists of a volumetric force generated in the medium during the propagation of a compression wave by momentum transfer with the medium) have thus been developed over the past twenty years.

These solutions are based on the following physical principle. Focusing a high-intensity ultrasonic beam gives rise to non-linear effects resulting in a force acting on the medium at the focus point. If the ultrasound energy is delivered over a short instant (ms fraction), it results in a transient point stress which generates a shear wave with partial spherical symmetry around the focus point.

In these different solutions:
the excitation means for generating a shear wave, and
the means for generating high-frequency ultrasonic waves to image the tissue result from the use of a single component, namely the transducer array.

This transducer array is then able to:
first, generate a high-intensity ultrasonic pulse inducing the production of a shear wave by non-linear effect,
second, generate high-frequency ultrasonic waves to image the tissue in order to study the propagation of the shear wave.

However, a disadvantage of this technique relates to the fact that the amplitude of the generated shear wave is low, and propagates spherically quickly losing the amplitude necessary for tissue movement by limiting the way in which it penetrates deep into the tissue, because it is a second-order effect.

To overcome this disadvantage, it has been proposed to emit ultrasound being focused successively at different depths to create pushes by radiation pressure. The constructive shear wave interference thus produced forms a supersonic "Mach cone" (in which the speed of the source is greater than that of the generated wave) and a conical shear wave is created. The transducer array then switches to an ultrafast imaging mode (where high-frequency ultrasonic waves are generated) to follow the shear wave as it propagates through the medium.

Although this technique allows to obtain a conical shear wave by using the ultrasound imaging transducer itself, it has the disadvantage of being costly in terms of energy.

3. Purpose of the Invention

In summary:
the mechanical exciters proposed in the literature have unthinkable ergonomic features for a commercial product, and in particular for a product intended for the evaluation of hepatic fibrosis,
the acoustic exciters (using the force of radiation to produce the shear wave) have a very low electromechanical efficiency not possible for an ultraportable product with low energy consumption.

An object of the present invention is to propose an ultrasound imaging system allowing to overcome at least one of the aforementioned disadvantages.

More specifically, an object of the present invention is to provide a 2D pulse elastography system allowing, by minimizing the energy required to produce a shear wave, to measure the viscoelastic properties of a tissue.

BRIEF DESCRIPTION OF THE INVENTION

To this end, the invention proposes a probe for measuring the viscoelastic properties of a medium, for example a human or animal biological tissue, such as a liver, said measurement consisting of:
generating at least one low-frequency elastic wave in the medium,
simultaneously with the generation of the low-frequency wave:

emitting high-frequency ultrasonic waves, and
receiving acoustic echoes due to the reflections of the ultrasonic waves in the medium,
the probe comprising:
a housing,
a transducer array, mechanically integral with the housing, for emitting high-frequency ultrasonic waves and receiving acoustic echoes,
at least one inertial vibration exciter for emitting the at least one low-frequency elastic wave, said and at least one exciter including:
a fixed part mechanically integral with the transducer array,
a mobile part capable of moving freely relative to the fixed part to produce vibrations in order to generate the low-frequency elastic wave,
at least one return spring extending between the fixed part and the mobile part,
remarkable in that the mass of the mobile part is comprised between 5 and 25% of the total weight of the probe, and in that the stiffness coefficient of said and at least one return spring is comprised between 300 kg·s² and 50 000 kg·s² so that the resonance frequency of the inertial vibration exciter is substantially equal to the frequency of the low-frequency elastic wave.

Thus, the mass (of the mobile part of the exciter) and the stiffness coefficient (of the return spring(s)) are selected within ranges corresponding to the family of exciters that can be used at their respective resonance frequency to emit an elastic wave in a frequency range of interest.

This mass and this stiffness coefficient are further determined so that the resonance frequency of the exciter is equal to the frequency of the elastic wave. More specifically, if it is desired that the probe emits an elastic wave of frequency "F", then the mass "m" of the mobile part of the exciter and the stiffness coefficient "k" of the spring(s) are selected so that $$F = \frac{1}{2\pi}\sqrt{\frac{k}{m}}.$$

In practice, to size the probe correctly, knowing the desired frequency "F" for the elastic wave, the stiffness coefficient "k" (respectively the mass "m") is fixed in the range comprised between 300 kg·s² and 50 000 kg·s² (respectively between 5 and 25% of the total weight of the probe), and the mass "m" (respectively the stiffness coefficient "k") is calculated so as to satisfy the equation $$m = \frac{k}{(2\pi F)^2}\left(\text{respectively } k = m(2\pi F)^2\right).$$

In the context of the present invention, the term "free movement of the mobile part of the exciter" is understood to mean the fact that the mobile part moves without undergoing any stress exerted by a force external to the exciter, such as a force exerted by the user while gripping the probe. In particular, the only stresses undergone by the mobile part during its movement are gravity and the force(s) exerted by the exciter, namely a mechanical return force (exerted by a return spring) and an electromagnetic force in the case of an electromagnet exciter.

As will emerge from the following description, the fixed part mechanically integral with the transducer array can be attached:

directly to the transducer array, that is to say be in physical contact with the transducer array, or indirectly to the transducer array, that is to say be in physical contact with a component of the probe other than the transducer array (such as for example a chassis or the housing of the probe), this component being fixed (itself directly or indirectly) to the transducer array.

In all cases, the mechanical securing of the fixed part to the transducer array induces the absence of relative movement of these two elements relative to each other.

Preferred but non-limiting aspects of the probe according to the invention are the following:

each inertial vibration exciter may be devoid of a guiding slide cooperating by friction with a guide rod to ensure the movement of the mobile part in translation, said and at least one return spring forming a guide for the movement of the mobile part relative to the fixed part;

the probe may also comprise a controller for applying an electrical excitation signal allowing to drive the movement of the mobile part relative to the fixed part, the mobile part including at least one permanent magnet;

each inertial vibration exciter may also comprise an additional inertial mass distributed around the permanent magnet;

the additional inertial mass may comprise at least one side wall wound around a winding axis extending perpendicularly to a compression segment of the return spring, said and at least one side wall surrounding said compression segment;

alternatively, the additional inertial mass may have an axis of symmetry parallel to a compression segment of the return spring and be distributed around the permanent magnet;

further alternatively, the probe can also comprise at least one electronic acquisition card, the additional inertial mass consisting of said electronic card mechanically integral with the permanent magnet;

the probe may comprise several inertial vibration exciters driven by the controller, each exciter comprising a respective return spring, each return spring having a stiffness coefficient different from the stiffness coefficients of the other return springs;

the inertial vibration exciter may also include a damping layer disposed between the fixed part and the mobile part, said damping layer being made of a shock-absorbing material;

the controller may be adapted to apply an attenuation signal to each inertial vibration exciter in order to dampen an oscillation of the mobile part of each inertial vibration exciter relative to the fixed part of said inertial vibration exciter, said attenuation signal being calculated as a function of information representative of a relative movement between the probe and the medium of interest (from the processing of the acoustic echoes received and/or from a measurement of an electric current flowing in the exciter), alternatively, the controller can be programmed to apply an electrical excitation signal to each exciter in order to induce the oscillation of the mobile part of each exciter, without subsequent application of an attenuation signal, so as to allow the mobile part of each exciter to oscillate freely.

BRIEF DESCRIPTION OF THE DRAWINGS

Other advantages and features of the probe according to the invention will emerge better from the description which will follow of several variant embodiments, given by way of non-limiting examples, from the appended drawings in which.

DETAILED DESCRIPTION OF THE INVENTION

Figure 1:
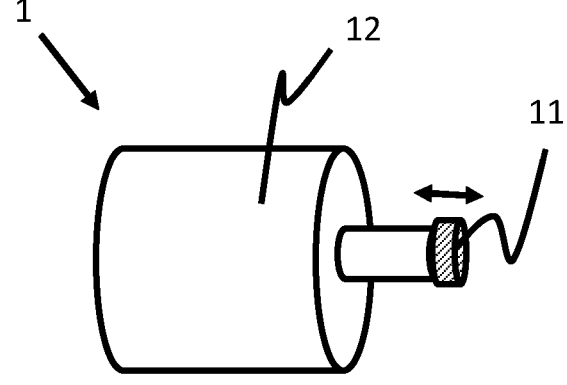
FIG. 1 is a schematic representation of an ultrasound pulse elastography medical apparatus of the prior art.

Different embodiments of the probe according to the invention will now be described in more detail with reference to the figures. In these various figures, the equivalent elements are designated by the same reference numeral.

1. GENERALITIES

Figure 3:
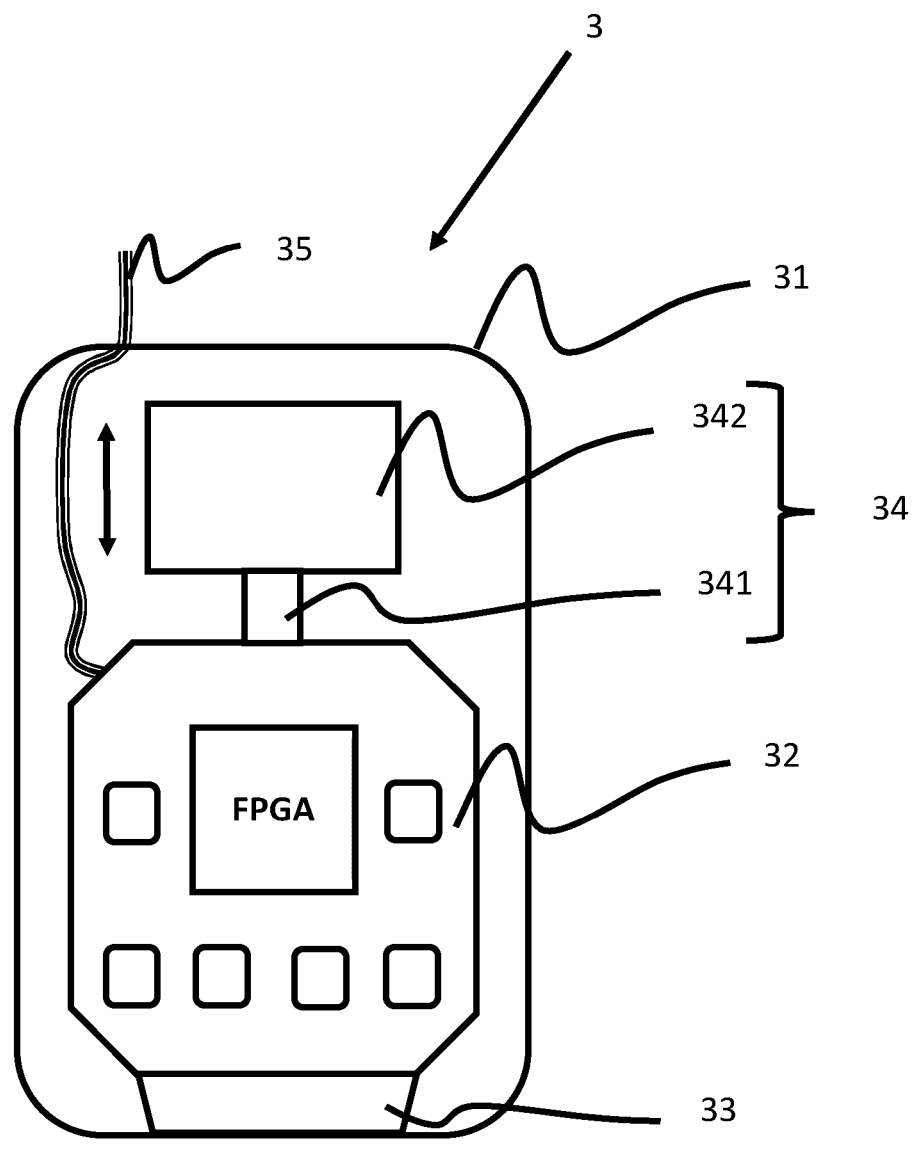
FIG. 3 is a schematic representation of a first embodiment of an ultrasonic pulse elastography probe according to the invention.

With reference to FIG. 3, an example of an ultrasonic pulse elastography probe according to the invention was illustrated. Such a probe allows the measurement of the elasticity of a tissue or of a human/animal organ.

The probe 3 comprises:
a housing 31
an electronic acquisition card 32 (optional),
a transducer array 33, and
an inertial vibration exciter 34 including a fixed part 341 and a mobile part 342 connected to each other by a return spring (not shown in FIG. 3).

The exciter 34 allows to generate vibrations. As will be described in more detail below, the fixed part of the exciter 34 is mechanically integral with the transducer array 33 to transmit the vibrations to the probe 3 in order to mechanically produce the shear wave necessary for the measurement of the viscoelastic properties of the tissue to be analyzed.

Figure 2:
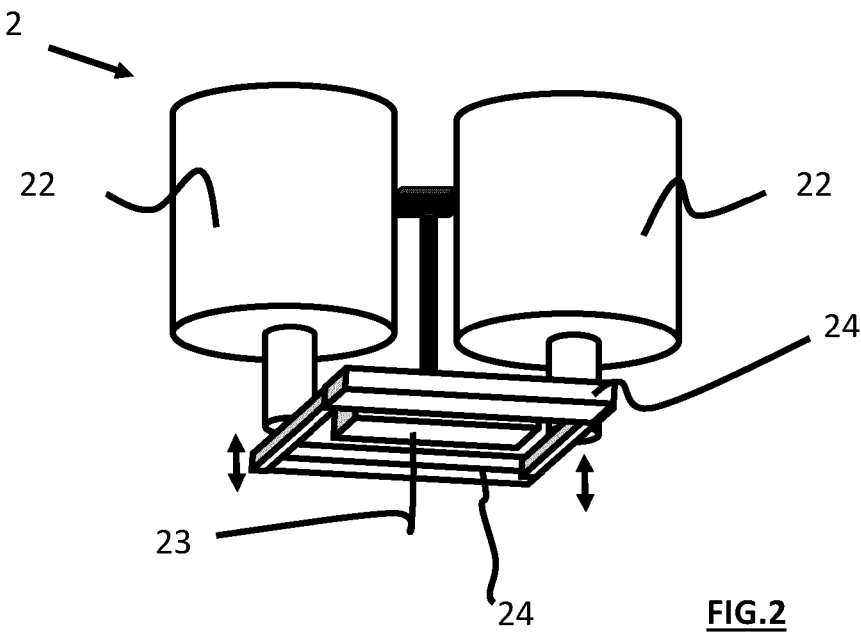
FIG. 2 is a schematic representation of a pulse elastography system of the prior art.

The use of an inertial vibration exciter 34 allows to obtain a probe in which the mass of the mobile part 342 generating the vibrations represents only 5 to 25% of the total mass of the probe, unlike the probe according to EP 3 315 074 as well as the apparatus and system illustrated in FIGS. 1 and 2 in which the bulk of the mass of the probe is concentrated in the mechanical exciter. This limits the weight and bulk of the probe according to the invention.

Moreover, the reader will appreciate that, as illustrated in FIGS. 9, 10, 11 and 13, the inertial vibration exciter 34 is not necessarily arranged so as to induce movement of the probe along an axis of symmetry of the transducer array 33. Indeed, in many embodiments, the axis of symmetry of the transducer array 33 and the axis of movement of the mobile part of the inertial vibration exciter 34 are not coincident. This allows to limit the size of the probe according to the invention.

The use of an inertial vibration exciter 34 further allows to generate a shear wave of sufficient power to measure the tissue viscoelastic properties while consuming less energy than that necessary for solutions based on ultrasonic radiation pressure.

1.1. Housing

The housing 31 of the probe 3 accommodates the probe acquisition means as well as the shear wave generation means. More specifically, the optional electronic card 32, the transducer array 33 and the inertial vibration exciter 34 are housed in the housing 31.

An advantage of such a probe is that all the mobile parts of the probe (in particular the mobile part of the inertial vibration exciter 34) are internal to the housing 31 and therefore protected. This facilitates the disinfection of the probe 3. Seen from the outside, the probe is non-deformable, which solves many problems of usability and facilitates its gripping by the user.

The probe also comprises (wired or wireless) communication means 35 for sending the acquired data (optionally preprocessed and beamformed) to a calculation unit (remote computer and/or tablet and/or smartphone, etc.) for the reconstruction of elementary images of a target object and/or the estimation and/or the display of the elasticity of the target object.

1.2. Transducer Array

The transducer array 33 comprises a set of "n" ultrasonic transducers ("n" being an integer greater than or equal to one) disposed linearly, or in a curve, or in concentric circles, or in a matrix.

The transducer array 33 allows to emit ultrasonic excitation waves towards a medium to be explored (organ, biological tissue, etc.), and to receive acoustic echoes (that is to say ultrasonic waves reflected by the various interfaces of the medium to be explored). Each transducer consists for example of a plate of piezoelectric material of rectangular shape coated on its front and rear faces with electrodes. Such transducers are known to the person skilled in the art and will not be described in more detail below.

In the variant embodiment illustrated in FIG. 3, all transducers of the array are used both in emission and in reception. In other embodiments, separate transducers may be used for emission and reception.

1.3. Electronic Card

The optional electronic card 32 is connected to the transducer array 33. It allows to control the transducers of the array, and to process the data acquired by the transducers of the array. More specifically, the acquisition electronic card 32 allows:

- to command the transducers to emit ultrasonic waves towards the medium to be explored,
- to command the transducers to receive the echoes reflected by the various interfaces of the medium to be explored,
- to pre-process the echo signals and to transmit them to the remote calculation unit.

The electronic card can also comprise a controller to drive the inertial vibration exciter 34, as will be described in more detail below.

1.4. Inertial Vibration Exciter

The inertial vibration exciter 34 allows to vibrate the probe 3 to induce the generation of a shear wave.

More specifically, the movement of the mobile part 342— or "inertial mass"—of the exciter 34 in the direction opposite to that of the desired movement moves the transducer array 33 in the other direction, and produces the desired shear wave.

Advantageously in the context of the present invention, it is the fixed part 341 of the exciter 34 which is ("directly" or "indirectly") mechanically integral with the transducer array 33, unlike the solutions of the prior art. Indeed:

- in the elastography apparatus 1 illustrated in FIG. 1, the transducer 11 is integral with the mobile part of the electrodynamic actuator 12, the other part, which is fixed, of the actuator being held in the hand by the user
- in the elastography system 2 illustrated in FIG. 2, the set of transduction elements 23 is totally separated from the mechanical excitation means 22, 24 (the vibration generated by the mechanical excitation means 22, 24 is not transmitted to the set of transducer elements 23).

This particular arrangement (use of an inertial vibration exciter 34 whose fixed part 341 is connected to the transducer array 33 to make it vibrate) allows to generate a shear wave of acceptable strength with:

- a probe having a minimal bulk (volume substantially identical to that of a probe using the radiation force),
- a probe consuming limited energy to generate the shear wave. The source of energy necessary for the excitation of the actuator 34 can moreover be provided by a battery embedded in the probe, when the communication link 35 is wireless.

In other words, the proposed solution has the advantages of the two technologies of the prior art without their respective disadvantages, namely:

- a high shear wave generation yield (just like mechanical shear wave generation solutions), and
- a small bulk (just like acoustic shear wave generation solutions).
- a slightly increased weight (not more than 25%, in particular 20%) compared to this same probe without inertial vibration exciter.

In the embodiment illustrated in FIG. 3, all the elements disposed inside the housing 31 are mechanically integral with the exception of the mobile part 342.

These mechanically integral elements (that is to say housing 31, electronic card 32, transducer array 33 and fixed part 341 of the exciter 34) constitute a single mass, of the order of 200 to 300 grams.

The mobile part 342 of the exciter 34 (forming an inertial mass) has a mass comprised between 25 and 50 grams (and more generally from 5 to 25% of the weight of the probe). The fact that the mass of the mobile part 342 is comprised between 25 and 50 grams (and more generally from 5 to 25% of the total weight of the probe) allows to have an inertial mass:

high enough to guarantee the shear wave generation efficiency, low enough not to excessively increase the weight of the probe and thus ensure its handling.

The inertial vibration exciter is adapted to be used at its resonance frequency. More specifically:

the mass of the mobile part of the exciter and the stiffness coefficient of the return spring (or the total stiffness coefficient of the return springs)

are chosen so that the resonance frequency of the exciter matches the desired frequency for the shear wave.

In particular:

the mass of the mobile part is comprised between 5 and 25% of the total weight of the probe, and the stiffness coefficient of the return spring(s) is comprised between 300 kg·s$^2$ and 50 000 kg·s$^2$, preferably 1 000 kg·s$^2$ and 10 000 kg·s$^2$, and even more preferably between 4 000 kg·s$^2$ and 6 000 kg·s$^2$.

The fact that provision is made to operate the exciter at its resonance frequency allows to limit the amount of energy necessary for the generation of the shear waves. By limiting the energy consumption of the exciter, it is then possible to power supply the probe by battery.

2. EXCITER

2.1. First Variant Embodiment of the Exciter

Figures 4, 5:
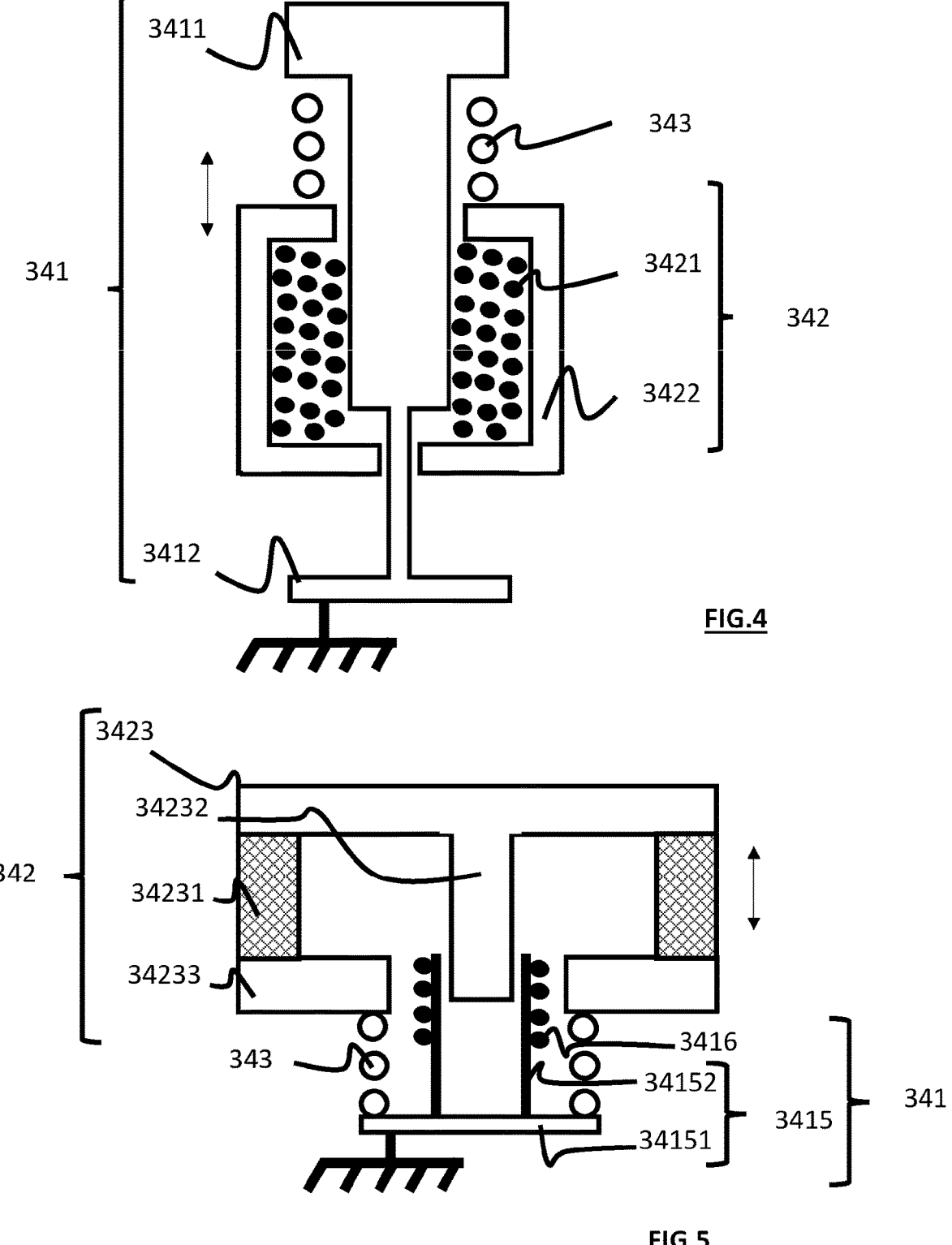
FIG. 4 is a schematic representation of a first exciter variant.
FIG. 5 is a schematic representation of a second exciter variant.

With reference to FIG. 4, a first variant embodiment of the exciter (based on the principle of the electromagnet and the plunger rod) is illustrated in which:

the fixed part 341 includes a rod called "plunger" rod including:

a head 3411 at one of its ends, for example made of mild steel, and a base 3412 at its other end, the base 3412 being intended to be directly or indirectly attached to the housing 31 (for example via the electronic card 32), and the mobile part 342 is composed of an electromagnet including:

an electrically conductive winding 3421 (for example made of copper), a magnetic core 3422 (for example made of mild steel) extending around the rod and channeling the magnetic field lines, the return spring 343 extends between the head 3411 and the magnetic core 3422.

The plunger rod is slidably mounted inside a through conduit formed in the magnetic core 3422. The operating principle of electromagnet and plunger rod exciters is as follows.

When an electric current is applied in the winding 3421, the ferromagnetic material of the head 3411 is suddenly attracted downwards, which induces a "plunge" of the rod inside the through conduit of the magnetic core 3422. The head 3411 moves down, and the return spring 343 is compressed. As soon as the winding 3421 is no longer supplied with electric current, the return spring 343 returns the sliding rod to the "high" position.

In the present case, the base 3412 of the plunger rod being (directly or indirectly) attached to the housing 31 of the probe 3, it is the magnetic core 3422 which moves towards the head 3411 by compressing the spring 343 when applying an electric current to the winding 3421. After interruption of this electric current, the magnetic core 3422 returns to the "low" position due to the force applied by the return spring 343.

It is then possible to obtain a reciprocating movement of the magnetic core 3422 depending on whether the electric current is applied or interrupted in the winding 3421. This reciprocating movement of the magnetic core 3422 induces the vibration of the whole probe 3, which allows to produce a shear wave.

Preferably, the electrical excitation should be close to a Dirac (a few milliseconds in duration).

A disadvantage of this type of exciter 34 is that it is difficult to finely control the movement of the magnetic core 3422:

under the effect of the application of the electric current, the magnetic core 3422 moves towards the head 3411 of the rod by compressing the spring 343, the continuation of the kinematics is exerted in the absence of electromagnetic force and results in an oscillation of the magnetic core 3422 with a pulsation depending on its mass and the stiffness of the spring 343.

It is therefore the stiffness of the spring 343 which will set the frequency of the movements of the magnetic core 3422: there is no means of finely controlling the excitation, nor of damping it. Moreover, the magnetic force developed in such a system is very dependent on the penetration of the rod into the magnetic core 3422, becoming maximum when the rod contacts the magnetic core 3422.

Another disadvantage of this type of exciter relates to guiding the translational movement of the plunger rod. In particular, the friction associated with the movement of the plunger rod inside the conduit—forming a guiding slide—induce frictional damping. Such frictional damping of the mobile part has the disadvantage of being uncontrolled, variable over time and highly dependent on the orientation of the probe.

This is why the inventors have proposed other variant embodiments (described below) in which the inertial vibration exciter has no guiding slide cooperating by friction with a rod to ensure the translational movement of the mobile part. This allows to have an inertial vibration exciter which has the advantage of having an intrinsic oscillatory behavior that is invariable in time and in space.

In these different variants described below, the guiding of the (translational or rotational) movement of the mobile part is ensured by one (or more) return spring(s) 343 extending between the fixed part 341 and the mobile part 342.

2.2. Second Variant Embodiment of the Exciter

A second variant of exciter allowing more control is illustrated with reference to FIG. 5. This exciter 34 still uses electromagnetic forces, but works with a magnetic system polarized by a permanent magnet.

More specifically:

the fixed part 341 of the exciter 34 comprises:

a carcass 3415 including:

a base 34151 intended to be (directly or indirectly) attached to the housing 31, a tubular support 34152 projecting perpendicularly to the base 34151, the tubular support 34152 including a central conduit, an electrical activation coil 3416 mounted on the tubular support 34152, the mobile part 342 of the exciter 34 comprises an armature 3423 arranged to partially surround the carcass 3415, the armature 3423 including:

an annular permanent magnet 34231, and an axial tubular guide 34232 made of mild steel intended to be slidably mounted inside the central conduit of the tubular support 34152, an annular pole piece 34233 made of mild steel surrounding the tubular support 34152 and the winding 3416 to define a magnetic air gap with the tubular guide 34232, the return spring 343 extends between the base 34151 and the armature 34233.

This exciter can be driven by a controller (not shown), for example integrated into the electronic card 32. This controller allows to emit an electrical excitation signal (from a few milliseconds to a few tens of milliseconds) to power supply the activation coil 3416 of the exciter 34 whose operating principle is as follows.

The activation coil 3416 mechanically attached to the housing 31 evolves in the air gap of the armature 3423 continuously biased by the annular permanent magnet 34231.

When the activation coil 3416 is power supplied with electric current (that is to say when the controller emits the electric excitation signal), it applies to the armature 3423 a vertical electromagnetic force proportional to the electric current, and whose direction (towards the base 34151 or opposite the base 34151), depends on the direction of the electric current.

This force induces the translational movement of the mobile part 342 along the central conduit (of the tubular support 34152) of the fixed part 341. More specifically, depending on the direction of the electric current, this force will:

either induce the translational movement of the mobile part towards the base 34151 of the fixed part so that the return spring 343 compresses, or induce the translational movement of the mobile part 342 in a direction opposite to the base 34151 of the fixed part 341 so that the return spring 343 stretches.

After interruption of the electric current, the mobile part 342 returns to its initial position, by oscillating due to the return spring 343 which successively compresses and stretches until it returns to its rest position. It is then possible to obtain a back and forth movement of the mobile part 342 depending on whether the electric current is applied or interrupted in the activation coil 3416. This back and forth movement of the mobile part 342 induces the vibration of the whole probe 3 by reaction, which allows to produce a shear wave when the probe 3 is in contact with a tissue.

Such devices exist commercially and are called audio exciters. As an indication, FIG. 6 illustrates an example of a commercial audio exciter (Tectonic product reference TEAX 14C02-8) including the features of the inertial exciter of FIG. 5.

Figures 6, 7A, 7B:
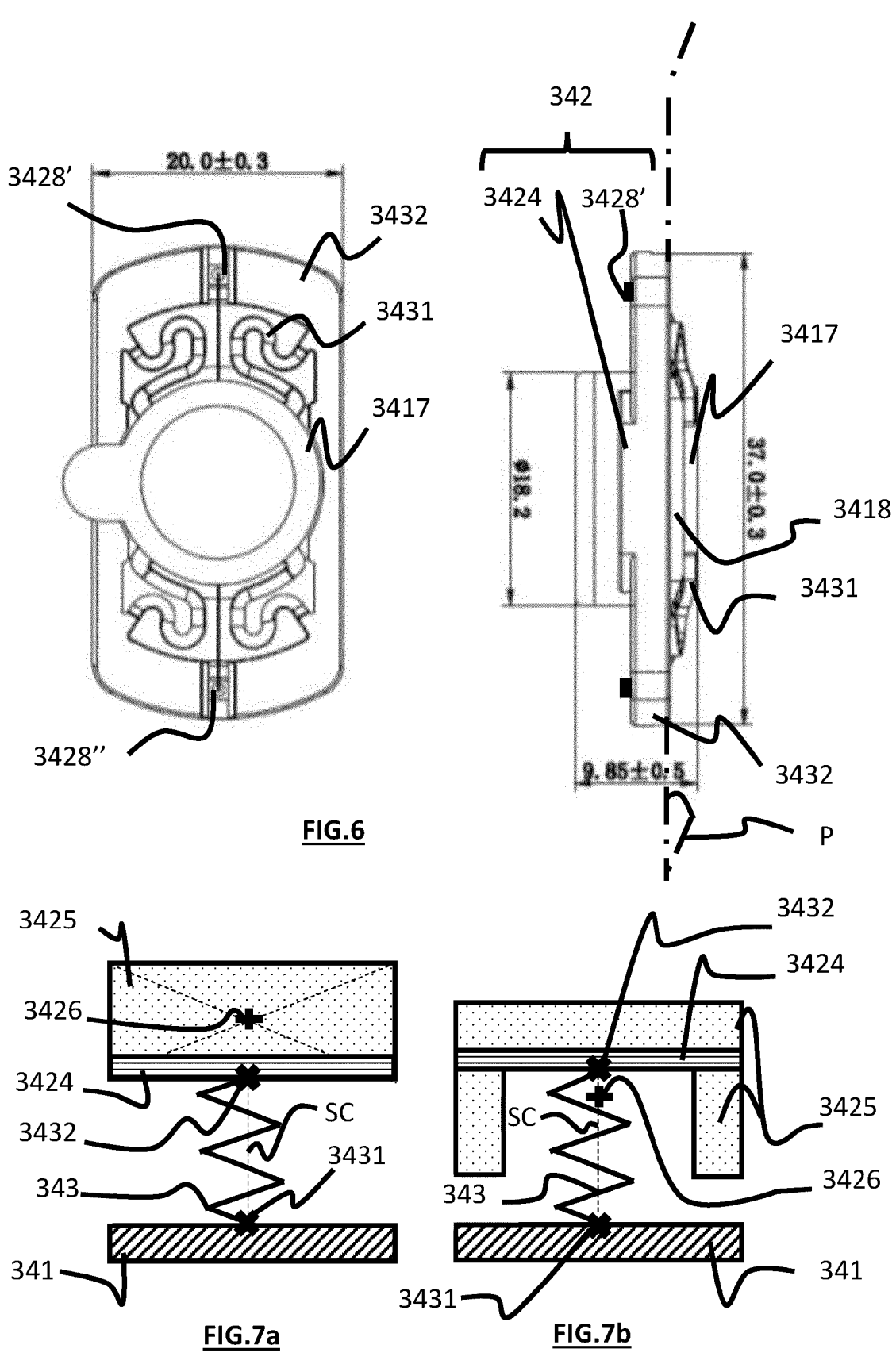
FIG. 6 is a schematic representation of an example of an exciter according to the second variant.
FIG. 7a is a schematic representation of a third exciter variant.
FIG. 7b is a schematic representation of a fourth exciter variant.

With reference to FIG. 6, this audio exciter comprises:

a circular ring 3417 forming a base, the outer face of the ring 3417 being covered with an adhesive layer, an induction coil 3418 on the inner face of the ring 3417, four self-recovering elastic lugs 3431 forming a return spring and projecting outwards from the ring 3417, a substantially rectangular frame 3432 forming an armature, the end of each elastic lug 3431 opposite the ring 3417 being connected to a respective corner of the frame 3432, a magnetic circuit biased by a permanent magnet 3424 attached to the edges of the larger frame electrical connectors 3428', 3428" for electrically connecting the induction coil 3418 to a current source (not shown).

Such an audio exciter is adapted to be attached on a support—such as a resonant plate—and to cause it to vibrate by inertia. The dimensions of this example of a commercial audio exciter are compatible with the width and thickness of the electronic cards used in existing probes. The force generated under an electric current of 1 A is 2.4 Newtons. The mass of the mobile part of such an exciter is 12.8 grams and oscillates at 100 Hz (for a total weight of the probe of 235 grams).

Thus, to cause such an exciter to oscillate at a resonance frequency of 50 Hz, it is necessary to increase the mass of the mobile part to 51.2 grams, for example by attaching an additional inertial mass of 38.4 grams to the permanent magnet 3424.

This additional inertial mass 3425 can be attached on the upper face of the permanent magnet 3424 as illustrated in FIG. 7a. This induces a modification of the position of the gravity center 3426 of the mobile part 342 of the exciter 34, the gravity center 3426 then being located outside a fixing plane of the mobile part containing the fixing point(s) of the end(s) of the return spring(s) opposite to the mobile part. In the context of the present invention, the term "ends of the return spring" is understood to mean:

if the return spring consists of a single self-recovering elastic element: the two tips of the elastic element, if the return spring consists of a plurality of self-recovering elastic elements, central points located at equal distance from the tips of said elastic elements respectively connected to either one of the fixed and mobile parts:

a first central point located at equal distance from the tips of the elastic elements connected to the fixed part 341 forming a first end of the return spring 343, and a second central point located at equal distance from the tips of the elastic elements connected to the mobile part 342 forming a second end of the return spring 343.

As a variant and as illustrated in FIG. 7b, the additional inertial mass 3425 can be distributed around the return spring 343, so that the center of gravity 3426 of the mobile part 342 is located close to the fixing plane P of the mobile part.

Figure 7C:
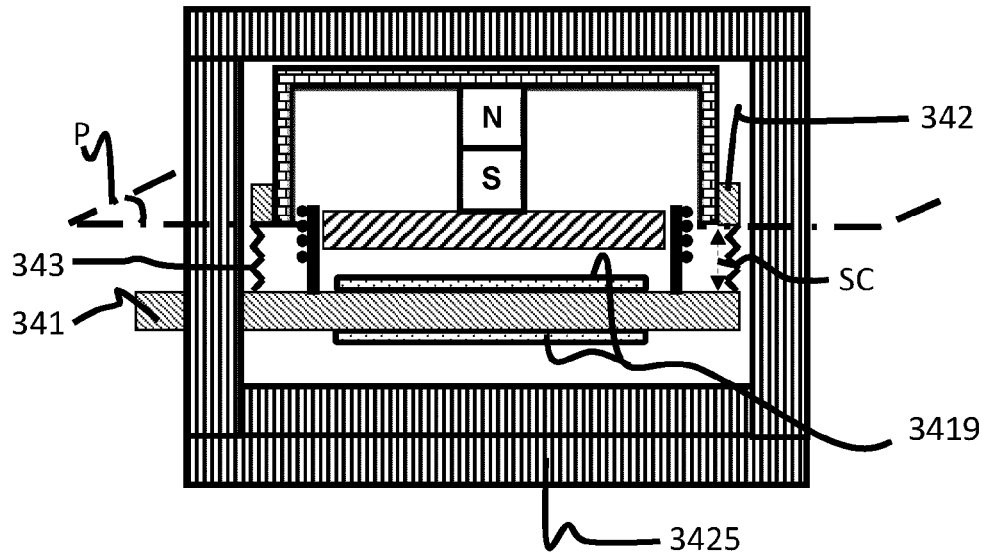
FIG. 7c is a schematic representation of a fifth exciter variant.

In the embodiment illustrated in FIG. 7c, the additional inertial mass is distributed all around the mobile part 342. More specifically in this embodiment, the additional inertial mass comprises a side wall. This side wall is wound around a winding axis extending perpendicularly to the compression segment SC of the return spring(s) 343, the side wall surrounding the compression segment SC. This allows to limit the bulk of the exciter. Moreover, in this embodiment, the exciter comprises a damping layer 3419 disposed between the fixed part 341 and the mobile part 342. This damping layer being made of a shock-absorbing material. This allows to limit the risks of damage to the exciter in the event of the probe falling. Alternatively, the additional inertial mass may have an axis of symmetry parallel to a compression segment of the return spring and be distributed around the permanent magnet. This allows to reduce the height of the exciter (in the direction of movement of the mobile part), and therefore to limit the bulk of the ultrasound pulse elastography probe.

As indicated previously, each time an excitation signal is applied by the controller, the mobile part 342 of the exciter 34 oscillates relative to the fixed part 341 until it returns to its initial rest position. Advantageously, the vibration of the mobile part 342—in particular the oscillation of the mobile part caused by the return spring 343 until it returns to its initial rest position—can be attenuated ("damping") by the controller to allow optimal control of the mechanical excitation. This attenuation can be adaptive. In particular, the attenuation can adapt to variations in the damping provided by the contact between the probe and the patient's body. For this purpose, it is necessary to know the real movements of the probe. This knowledge of the real movements of the probe can be obtained by various direct or indirect means. For example, these movements can be determined without using a specific position sensor:

either by processing the acoustic echoes received by the transducer array (the ultrasound movement film during and after the mechanical excitation can give a precise value of the relative movement between the probe and the tissue), or by using, after the electrical excitation phase, the signal amplified by a current amplifier from the exciter coil. This signal is representative of the relative movements of the mobile part of the exciter 34 and of the probe 31. When it is zero, this means that the mobile part, and therefore the probe, no longer oscillates.

Preferably, the device according to the invention uses information representative of the relative movement between the probe and the tissue (from the processing of the acoustic echoes received and/or from a measurement of an electric current flowing in the exciter coil) to calculate a signal allowing to attenuate the oscillation of the mobile part. This allows more effective attenuation of the oscillations of the mobile part than with information representative of the absolute movement of the probe.

Of course, the vibration of the mobile part 342 may not be attenuated. In this case, each time an excitation signal is applied by the controller, the mobile part 342 of the exciter 34 oscillates freely. This free oscillation causes the probe to move until the mobile part has returned to its initial rest position.

The movement of the probe (related to the free oscillation of the exciter) can be separated from the expression of the progress of the shear wave by digital filtering of the acquired data. Indeed, in the context of the present invention, the application of a post-processing allows to separate the movement of the probe from the expression of the movement of the shear wave. The fact of not attenuating the oscillation of the mobile part allows to reduce the electrical energy consumed by the probe. Indeed, in the case of a probe in which the oscillations of the mobile part of the exciter are attenuated, it is necessary:

to use an electrical excitation signal of higher strength to obtain a shear wave whose energy is equivalent to that of a shear wave obtained from a probe in which the oscillations of the mobile part of the exciter are not attenuated, to apply an electrical attenuation signal whose energy is non-zero to dampen the oscillations of the mobile part.

2.3. Remarks Concerning the Embodiments of FIGS. 7a to 7c

Due to the absence of a guiding slide cooperating by friction with a guide rod to ensure the translational movement of the mobile part, the embodiments of the exciter illustrated in FIGS. 7a to 7c have the advantage of having an intrinsic oscillatory behavior that is more stable in time and space. In these various embodiments, the (or some or each) return spring(s) form(s) a movement guide for the mobile part, which reduces friction and minimizes the oscillation damping phenomenon.

Such exciters are excited at the resonance frequency, which allows to limit the energy consumed by the exciter to generate the shear wave, unlike in particular the vibrator described in EP 3 315 074.

2.4. Theory Relating to the Invention

Figure 8:
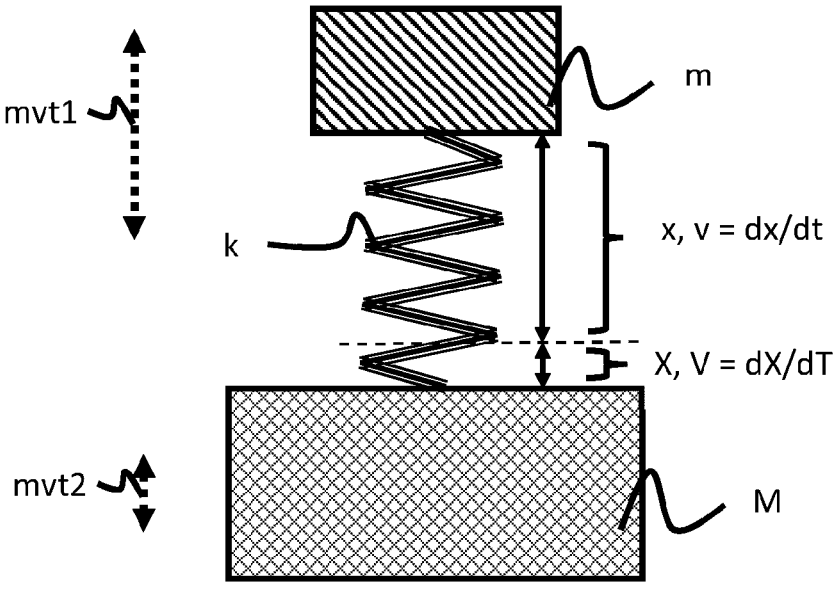
FIG. 8 is a block diagram of an exciter.

The different variant embodiments of the exciter 34 illustrated in FIGS. 4, 5, 6 and 7a, 7b can be represented by the block diagram illustrated in FIG. 8.

In this figure:

the mass "m" represents the mobile part 342 of the exciter 34; is noted "v" the instantaneous speed of the mass "m", and "x" its position, the mass "M" represents:

the fixed part 341 of the exciter 34 as well as the other components of the probe (housing, transducers, electronic card, etc.);

this mass "M" is typically comprised between 200 and 300 grams; is noted "V" the instantaneous speed of the mass "M", and "X" its position, the stiffness coefficient "k" represents the return spring 343.

The reader will appreciate that it is difficult to define an effective mass associated with the real mass "M" since such an effective mass depends in particular on:

the force with which the probe is gripped in the hand, the type of contact between the hand and the probe (flexibility of the material constituting the gripping means of the probe), the tracking force applied by the probe to the tissue.

In the rest of the calculations, it will be considered that the effective mass associated with the mass "M" is equal to twice the real mass of "M" (that is to say an effective mass comprised between 400 and 600 grams).

At an instant $t_0=0$, the return spring is in its rest position. An impulsive force is applied to the probe which tends to separate the two masses "M" and "m" for a duration of a few milliseconds, and with a total energy E.

As the same force acts on the two masses with an opposite sign, it is possible to write:

$$M^*d(V)/d(t)=-m^*d(v)/d(t)$$

This equation remains true after the initial pulse when the return spring reacts to the separation of the two masses since it always exerts forces of the same amplitude and of opposite sign on the two masses "M" and "m". It is therefore possible to write:

$$d(M^*V+m^*v)/dt=0,$$

where: $M^*V+m^*v$=constant (which is nothing other than the law of conservation of momentum considered within the framework of the theory of jet propulsion).

We therefore obtain: v=M/m*V, and by integration:

$$x = M/m * X \tag{1}$$

The relationship between the terms of equation (1) indicates that the speeds and movements are in the inverse ratio of the masses. This relation further allows to verify a first coherence of the system: to obtain a movement of 0.1 mm of the mass "M", it is necessary to move the inertial mass "m" by 1 mm (which is ten times lighter than the mass "M"); such millimeter movement is realistic, especially using the audio exciter shown in FIG. 6.

At the level of the energy expended, it is possible to write:

$$E = \tfrac{1}{2} * M * V^2 + \tfrac{1}{2} * m * v^2.$$

Note $E_u$ the useful energy; with: $E_u = \tfrac{1}{2} * M * V^2$
Then:

$$E = E_u * (1 + m/M * (v/V)^2) = E_u(1 + M/m)$$

The energy efficiency $\xi$ is therefore:

$$\xi = m/(m+M) \tag{2}$$

If the masses "M" and "m" are in a ratio of 10, then the energy efficiency is 9%, which is lower than that of Fibroscan® (close to 100%), but much higher than that of "push" ultrasound (probably around $\tfrac{1}{1000}$). We are therefore still in the coherence of the system.

The absolute value of this energy will now be studied.

After the initial pulse the two masses "M" and "m" oscillate at a frequency corresponding to a pulse Ω.

The conventional relationship between the spring stiffness, k, and Ω can easily be demonstrated:

$$\Omega = \sqrt{/(k*(1/m + 1/M))} \tag{3}$$

Moreover: $v_{Max} = \Omega * x_{Max}$
Where:

$v_{Max}$ is the maximum value of the speed of the inertial mass "m", and $x_{Max}$ is the maximum value of the distance from the inertial mass "m".

The energy supplied to the probe therefore satisfies the following equation:

$$E = \tfrac{1}{2} * M * V^2 + \tfrac{1}{2} * m * v^2 = \tfrac{1}{2} * m/M * (m+M) * \Omega^2 * X_{Max}^2$$

In the particular case where:
the mass of "m" is the tenth of the mass of "M",
M=0.25 kg,
the frequency is 50 Hz, and
$x_{Max}$ IS 1 mm,
then the energy supplied is: E=0.5*0.1*0.275*(2*π*50*10⁻³)²=1.4 mJ This energy is very low compared to the amount of energy allocated to the operation of the probe (typically less than five Watts). Even if it has to be assumed that the effective mass is three times greater than that of the probe, and that consequently $x_{Max}$ must also be three times greater than 1 mm, then the energy required will only be worth ten times more, that is to say barely more than 10 mJ, which is still very reasonable.

In conclusion, the orders of magnitude in terms of:
inertial mass,
amplitude of movement of the inertial mass, and
energy to bring to the probe
are all reasonable and acceptable in order to generate the shear wave.

The use of an inertial vibration exciter allows to obtain a probe adapted to generate a shear wave having:
an energy efficiency much higher than that of "push" type solutions, and a much smaller bulk than that of solutions using mechanical excitation means such as Fibroscan®.

3. EXAMPLES OF EXCITER ARRANGEMENTS

FIG. 3 illustrated a first embodiment of the probe. As shown in FIGS. 9 to 12, the arrangement of the inertial vibration exciter 34 in the probe 3 can vary. Different embodiments of the probe will now be described in more detail with reference to these FIGS. 9 to 12.

3.1. Second Embodiment

An example of a probe 3 is illustrated with reference to FIG. 9, said probe comprising:
a housing 31
an electronic acquisition card 32,
a transducer array 33, and
a pair of inertial vibration exciters 34a, 34b.

Each exciter 34a, 34b includes a fixed part 341a, 341b and a mobile part 342a, 342b connected to each other by a return spring. The fixed part 341a, 341b of each exciter 34a, 34b is fixed to the edge of the electronic card 32 opposite the edge connected to the transducer array 33.

The inertial vibration exciters 34a, 34b can be driven by a controller, for example integrated into the electronic card 32. This controller allows to apply an electrical excitation signal (of a few milliseconds) to induce the generation of vibrations by the exciters 34a, 34b.

The advantage of this system is that:
if the two inertial exciters 34a, 34b are driven in phase by the controller (that is to say the activation signal is applied simultaneously to the two inertial vibration exciters 34a, 34b), then it is possible to generate a (vertical) translational movement of the probe,
if, on the other hand, the two inertial exciters 34a, 34b are controlled in phase opposition by the controller, then it is possible to generate a rotational movement of the probe with a main horizontal component in the plane of the transducer.

Of course, the reader will have understood that the exciters 34a, 34b can be controlled in configurations other than in phase or in phase opposition, for example to generate movements with an arbitrary and predetermined time variation. Furthermore, the reader will appreciate that the probe can comprise more than two inertial vibration exciters arranged at variable positions in the housing.

Finally, the reader will appreciate that the exciters can be arranged according to other variant embodiments. For example, in the embodiment illustrated in FIG. 12, the mobile part 342 comprises:
two magnetic motors each including in particular:
an activation coil 3416', 3416" and
a permanent magnet 3424', 3424",
two return springs 343', 343" of different stiffnesses k', k" (for example k'=2×k"), each spring being associated with a respective magnetic motor.

Two coupled oscillators are thus obtained. This allows to explore a wide range of oscillation frequencies in order to be able to evaluate the viscosity of the target object.

3.2. Third Embodiment

Figures 9, 10:
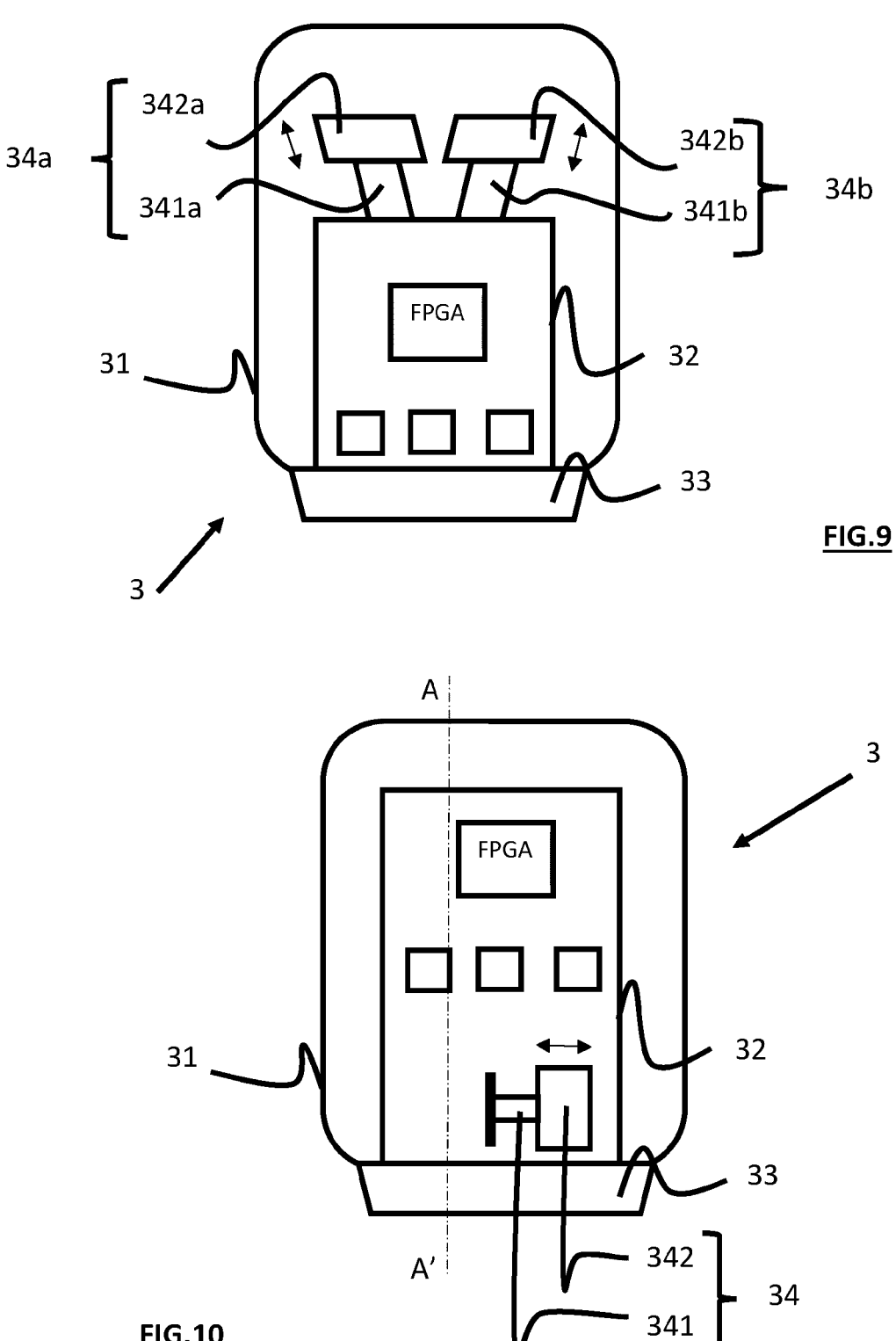
FIG. 9 is a schematic representation of a second embodiment of an ultrasonic pulse elastography probe according to the invention.
FIG. 10 is a schematic representation of a third embodiment of an ultrasonic pulse elastography probe according to the invention.

With reference to FIG. 10, another example of a probe 3 comprising:
a housing 31
an electronic acquisition card 32, a transducer array 33, and an inertial vibration exciter 34.

In this embodiment, the inertial vibration exciter 34 is:

positioned close to the transducer array 33 (that is to say at the edge of the electronic card connected to the transducer array), and is oriented so that the mobile part 342 vibrates in translation along a transverse axis perpendicular to a longitudinal axis A-A' of the probe 3, unlike the embodiment illustrated in FIG. 3 in which the inertial vibration exciter 34 is:

positioned at a distance from the transducer array 33 (that is to say at the edge of the electronic card opposite the transducer array 33) and is oriented so that the mobile part 342 moves in translation parallel to the longitudinal axis A-A' (that is to say perpendicular to a plane in which the transducers of the array 33 extend).

In this third embodiment, the positioning and orientation of the inertial vibration exciter 34 allow to generate movements of the mobile part 342 in the plane of the transducers of the array 33.

3.3. Fourth Embodiment

Figure 11:
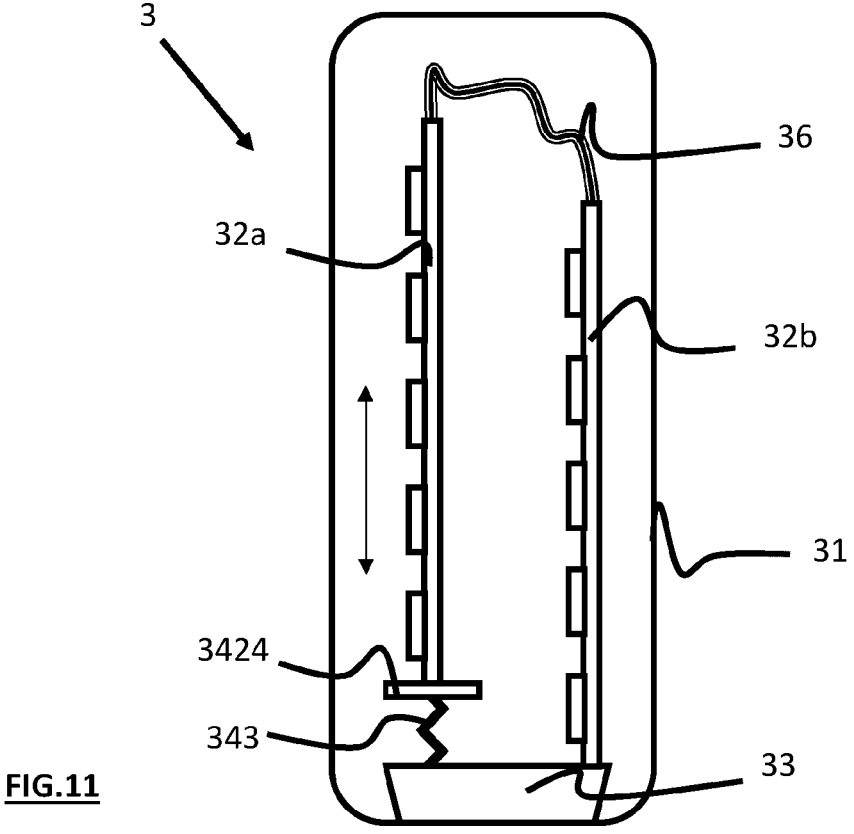
FIG. 11 is a schematic representation of a fourth embodiment of an ultrasonic pulse elastography probe according to the invention.
Figure 12:
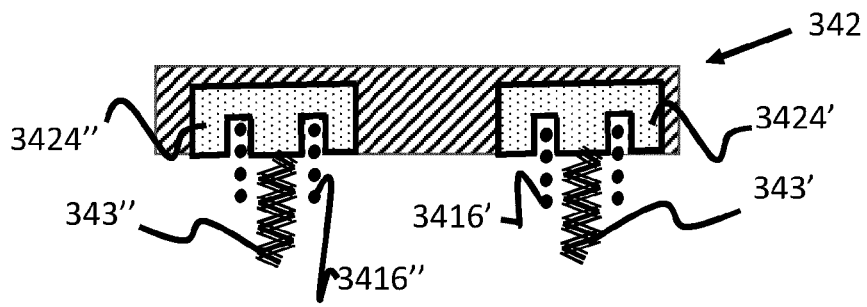
FIG. 12 is a schematic representation of a sixth exciter variant.

With reference to FIG. 11, another example of a probe was illustrated in which the additional inertial mass 3425 fixed to the permanent magnet 3424 of the exciter 34 consists of an electronic card 32a of the probe 3.

More specifically in this embodiment, the probe comprises:

a housing 31, first and second electronic acquisition cards 32a, 32b, said first and second electronic cards being electrically connected to each other by means of flexible connection cables 36, a transducer array 33, and an inertial vibration exciter 34 including:

a fixed part (not shown) mechanically integral with the transducer array 33, a mobile part including a magnetic circuit polarized by a permanent magnet 3424, and a return spring 343 between the fixed and mobile parts.

As illustrated in FIG. 11, the first electronic card 32a is mechanically integral with the permanent magnet 3424 of the exciter 34. Thus, the first electronic card 32a constitutes the additional inertial mass necessary to induce the vibration of the exciter 34 at a frequency of 50 Hz. This allows on the one hand to limit the size of the probe 3 and on the other hand to limit the increase in the weight of the probe by using one of its components to form the additional inertial mass.

The second electronic card 32b is, in turn, mechanically integral with the transducer array 33.

The principle of operation is as follows. When an activation signal (of a few milliseconds) is applied to the exciter 34, the permanent magnet 3424 and the first electronic card 32a move in translation in a direction opposite to the transducer array 33. The return spring 343 stretches. After interrupting the electrical activation signal, the return spring 343 applies a force to the magnet 3424 and the first electronic card 32a to bring them back towards the transducer array 33. The permanent magnet 3424 and the electronic card 32a move in translation towards the transducer array 33 and exceed their rest position so that the return spring 343 is compressed. The return spring then exerts on the permanent magnet 3424 (and the first electronic card 32a) a force tending to separate it from the transducer array. This damped oscillation continues until the permanent magnet and the electronic card return to their rest position.

To continue this vibration, it is possible to periodically apply the activation signal. A shear wave train is thus generated in the tissue when the probe is applied to the patient's skin.

3.4. Other Types of Exciter

Of course, other types of inertial vibration exciters can be used to allow the generation of the shear wave by the probe. For example, the probe including an inertial vibration exciter 34 with a motor driving an eccentric mass.

4. CONCLUSIONS

Regardless of the exciter 34 used or the arrangement retained for the probe 3, the principle of operation of the probe is as follows.

The actuator vibration exciter 34 is activated to induce the movement of the probe 3 in response to the movement of its mobile part 342 and generate a low-frequency elastic wave (the shear wave) in the tissue to be analyzed. Specifically, the controller emits an excitation signal to the exciter 34.

This signal induces the movement of the mobile part(s) relative to the fixed part(s) (simultaneously or successively, for example in phase opposition). When this signal (of a few milliseconds) is interrupted, the mobile part returns to its original position by oscillating—or not if the controller emits an attenuation signal to dampen the oscillation of the mobile part. The vibratory movement produced by the exciter is transmitted to the probe via the fixed part mechanically integral with the transducer array.

During the propagation of the low-frequency shear wave in the tissue in contact, the transducer array 33 emits and receives high-frequency ultrasonic waves in order to allow the study of the propagation of the low-frequency elastic wave.

The mode of generation of the shear wave proposed above is effective in the transmission of mechanical energy to the tissue, since the transducer array 33, in contact with the tissue, is directly moved by the inertial vibration exciter. It also allows to obtain a probe whose bulk is minimized.

Figure 13:
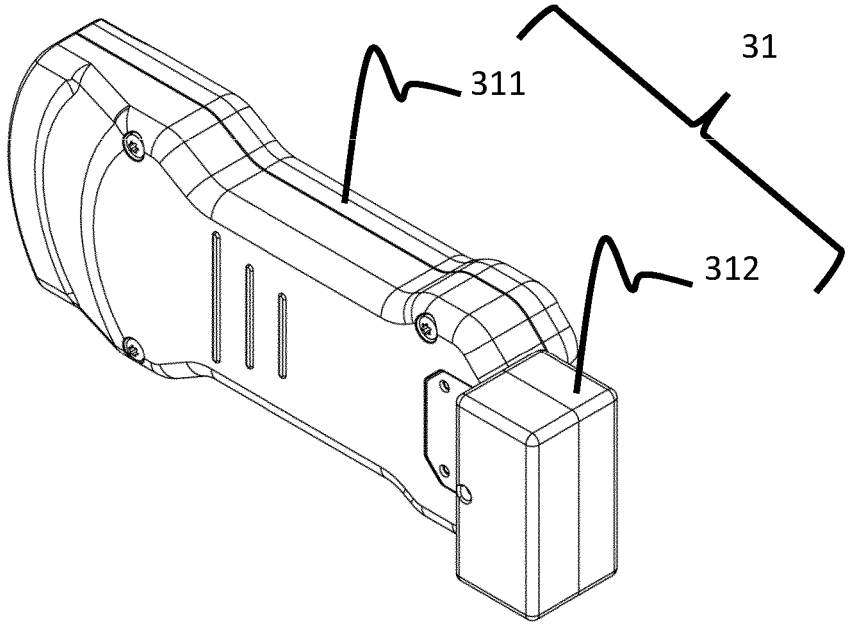
FIG. 13 is a perspective representation of an example of a probe according to the invention.

Different solutions can be considered for integrating the inertial vibration exciter described above into the probe. For example, said exciter may be incorporated into a secondary receptacle 312, as illustrated in FIG. 13. In this case, the housing 31 comprises:

a primary receptacle 311 integrating in particular the optional electronic acquisition card and the transducer array, the secondary receptacle 312, the secondary receptacle 312 being mechanically integral with the primary receptacle 311.

Figure 14:
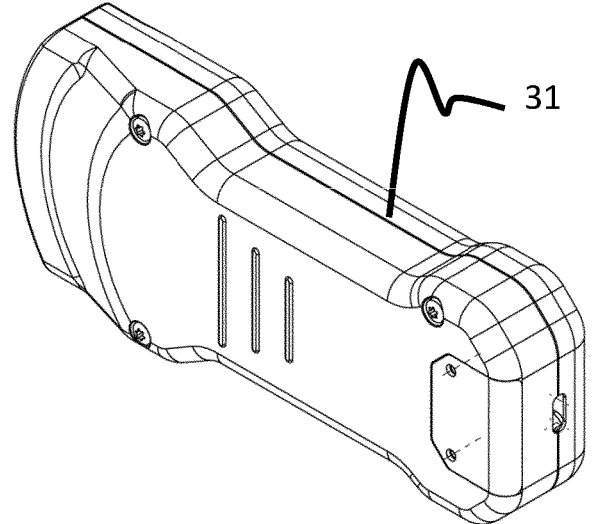
FIG. 14 is a perspective representation of another example of a probe according to the invention.

Alternatively, the inertial vibration exciter can be integrated into the housing 31 of the probe 3 (FIG. 14). In all cases, the inertial vibration exciter is integrally mounted with the transducer array, and no mobile part of the exciter is in contact with the user holding the probe, which allows its free oscillation. The handling of the probe by the user attenuates the amplitude of its vibration as induced by the exciter, but without however preventing the emission of shear waves in contact with a patient due to the elasticity of the tissues of the user's hand.

The reader will have understood that many modifications can be made to the invention described above without materially departing from the new teachings and advantages described here.

Accordingly, all such modifications are intended to be incorporated within the scope of the appended claims.

The invention claimed is:

1. A probe for measuring the viscoelastic properties of a medium, for example a human or animal biological tissue, such as a liver, said measurement consisting of:

generating at least one low-frequency elastic wave in the medium, simultaneously with the generation of the low-frequency wave:

emitting high-frequency ultrasonic waves, and receiving acoustic echoes due to the reflections of the ultrasonic waves in the medium, the probe including:

a housing, a transducer array, mechanically integral with the housing, for emitting high-frequency ultrasonic waves and receiving acoustic echoes, at least one inertial vibration exciter for emitting said and at least one low-frequency elastic wave, said and at least one exciter including:

a fixed part mechanically integral with the transducer array, a mobile part capable of moving freely relative to the fixed part to produce vibrations in order to generate the low-frequency elastic wave, at least one return spring extending between the fixed part and the mobile part, wherein the mass of the mobile part is comprised between 5 and 25% of the total weight of the probe, wherein the stiffness coefficient of said and at least one return spring is comprised between 300 kg·s$^2$ and 50 000 kg·s$^2$ so that the resonance frequency of the inertial vibration exciter is substantially equal to the frequency of the low-frequency elastic wave, wherein the probe further comprises a controller for applying an electrical excitation signal allowing to drive the movement of the mobile part relative to the fixed part, and wherein the mobile part includes at least one permanent magnet, each inertial vibration exciter including an additional inertial mass distributed around the permanent magnet.

2. The probe according to claim 1, wherein each inertial vibration exciter has no guiding slide cooperating by friction with a guide rod to ensure the translational movement of the mobile part, said and at least one return spring forming a guide for the movement of the mobile part relative to the fixed part.

3. The probe according to claim 1, wherein the additional inertial mass comprises at least one side wall wound around a winding axis extending perpendicularly to a compression segment of the return spring, wherein said and at least one side wall surrounds said compression segment.

4. The probe according to claim 1, wherein the additional inertial mass extends around an axis of symmetry parallel to a compression segment of the return spring, wherein said mass is distributed around the permanent magnet.

5. The probe according to claim 1, which further comprises at least one electronic acquisition card, wherein the additional inertial mass consists of said electronic card mechanically integral with the permanent magnet.

6. The probe according to claim 1, which comprises several inertial vibration exciters driven by the controller, wherein each exciter comprises a respective return spring, and wherein each return spring has a stiffness coefficient different from the stiffness coefficients of the other return springs.

7. The probe according to claim 1, wherein the inertial vibration exciter further includes a damping layer disposed between the fixed part and the mobile part, wherein said damping layer is made of a shock-absorbing material.

8. The probe according to claim 1, wherein the controller is adapted to apply an attenuation signal to each inertial vibration exciter in order to dampen an oscillation of the mobile part of each inertial vibration exciter relative to the fixed part of said inertial vibration exciter, said attenuation signal being calculated as a function of information representative of a relative movement between the probe and the medium of interest.

9. The probe according to claim 1, wherein the controller is programmed to apply an electrical excitation signal to each exciter in order to induce the oscillation of the mobile part of each exciter, without subsequent application of an attenuation signal, to allow the mobile part of each exciter to oscillate freely.

* * * * *